United States Patent
Madhukar et al.

(10) Patent No.: US 7,282,611 B1
(45) Date of Patent: Oct. 16, 2007

(54) PROCESS FOR THE PREPARATIONS OF A MIXTURE OF ALCOHOLS AND KETONES

(75) Inventors: Deshpande Raj Madhukar, Maharashtra (IN); Rane Vilas Hari, Maharashtra (IN); Chaudhari Raghunath Vithal, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 11/527,079

(22) Filed: Sep. 25, 2006

(30) Foreign Application Priority Data

Mar. 10, 2006 (IN) .................... 0656/DEL/2006

(51) Int. Cl.
*C07C 45/00* (2006.01)
*C07C 27/00* (2006.01)
*C07C 35/08* (2006.01)

(52) U.S. Cl. .............. 568/342; 568/344; 568/822; 568/876

(58) Field of Classification Search ............ None
See application file for complete search history.

(56) References Cited

U.S. PATENT DOCUMENTS

| | | | | |
|---|---|---|---|---|
| 3,660,504 A | * | 5/1972 | Oda et al. .......... | 568/821 |
| 4,459,427 A | * | 7/1984 | Middleton et al. .......... | 568/342 |
| 4,978,799 A | * | 12/1990 | Sanderson et al. .......... | 568/385 |
| 4,978,800 A | * | 12/1990 | Sanderson et al. .......... | 568/385 |
| 5,220,075 A | * | 6/1993 | Ember .......... | 568/573 |
| 5,767,320 A | * | 6/1998 | Raja et al. .......... | 568/360 |

OTHER PUBLICATIONS

Kim et al. Fe(TPA)-catalyzed alkane hydroxylation can be a metal-based oxidation. Journal of Molecular Catalysis A: Chemical, 1997, vol. 117, pp. 83-89.*

Fujiwara et al. Oxidation of alkanes by TBHP in the presence of soluble titanium complexes. Journal of Molecular Catalysis A: Chemical, 1999, vol. 142, pp. 77-84.*

* cited by examiner

*Primary Examiner*—Sikarl A. Witherspoon
(74) *Attorney, Agent, or Firm*—Abelman, Frayne & Schwab

(57) ABSTRACT

The present invention provides a process for the preparation of a mixture of alcohols and ketones by the liquid phase oxidation of isoalkanes to alkyl hydroperoxides with simultaneous transfer of oxygen to alkanes ($C_8$-$C_{20}$) in presence of oxides alkaline earth metals like magnesium, calcium, barium and strontium and oxides of rare earth metals such as lanthanum, cerium, samarium, neodymium and europium, at a temperature ranging between 110°-160° C. and air pressure ranging between 10-1500 psig for a period of 0.5-20 h, cooling the reaction mixture to 5° C., separating the products by conventional methods such as distillation. The catalyst reused for several times without affecting its catalytic performance.

13 Claims, No Drawings

PROCESS FOR THE PREPARATIONS OF A MIXTURE OF ALCOHOLS AND KETONES

FIELD OF INVENTION

The present invention relates to a process for the preparation of a mixture of alcohols and ketones. More particularly it relates to the said process comprising liquid phase oxidation of isoalkanes to alkyl hydroperoxides with simultaneous transfer of oxygen to alkanes in presence of oxides of alkaline earth and rare earth metal catalysts.

BACKGROUND OF THE INVENTION n-alkanes has a number of industrial applications as it can be used as feedstock for manufacture of numerous intermediates and finished products, such as alcohols and ketones, having tremendous demand in the manufacture of variety of industrially important products. The alcohols and ketones are either sulfonated or ethoxylated to different types of detergents. Fatty alcohols and their derivatives are of great commercial importance as surfactants, plasticizers, etc. The most widely used are $C_{12}$-$C_{16}$ fatty alcohols. In the literature, a number of studies have been reported on the oxidations of higher alkanes to alcohols and ketones via air or oxygen as an oxidant. Reactions of alkanes with alkyl hydroperoxide for the manufacture of alcohols and ketones have also been extensively studied in the literature. But there are no reports on the production of a mixture of alcohols and ketones by liquid phase oxidation of isopentane to alkyl hydroperoxide with simultaneous transfer of oxygen to alkanes.

The uses of palladium metal and palladium organometallic complexes for alkane oxidation are well known. A majority of literature reports on palladium catalyzed oxidation deal with lower alkane oxidation ranging from methane to butane using molecular oxygen, in a highly acidic medium. References may be made to the paper, Metallokompleksnyi Katal., 116-29, 1977 by Rudakov et al. wherein the oxidation of saturated hydrocarbons is reported using palladium (II) complexes as catalysts in highly acidic media like sulfuric acid, sulfuric acid-aluminum sulfate, and phosphoric acid-boron trifluoride. The disadvantage of this system is the essential requirement of a highly acidic medium, to conduct the reaction, which is avoided in the present invention. The present invention can be conducted without any solvent, and hence is avoid of any acidic/corrosive components.

References may be made to another paper, New J. Chem., 13(10-11), 761-6, 1989, by Herron et al., wherein zeolite supported Fe/Pd bimetallic catalysts are used for the selective oxidation of alkanes at room temperature. Here a mixture of hydrogen and oxygen, or $H_2O_2$ is used as an oxidant.

U.S. Pat. No. 5,235,117 teaches the preparation of boric acid and its use in the oxidation of saturated hydrocarbons to alcohols is reported. In the present invention the oxidation catalyst used is supported Pd catalyst, which catalyzes the alkane oxidation in the presence of alkyl hydroperoxide. No boric acid is employed in the present invention.

$PdSO_4.2H_2O$ is used as a catalyst in International Patent Appl. WO 9214738 A1 to convert methane to $MeOSO_3H$ in 20% oleum at 100° C. The process uses $PdSO_4$ as an oxidation catalyst for oxidation of methane to esters and alcohols in highly acidic medium is also reported. In the present invention, the catalyst used is a supported Pd catalyst and the reaction is carried out in a solvent, free from any acidic components.

A very high alcohol to ketone ratio was reported in the oxidation of cyclohexane with t-butyl hydroperoxide (TBHP) over Fe-tris[2-pyridyl methyl]amine catalyst. The alcohol: ketone ratio was 18, at an alkane conversion of ~30% [J. Kim et. al. J. Mol. Catal. A:Chem., 117, 83, (1997)]. The oxidation of cyclohexane by TBHP in the presence of titanium alkoxide produced the corresponding alcohols and ketones, whereas, other titanium complexes with titanyl or peroxo-titanium groups were not effective [(M Fujiwara et al., J. Mol. Catal. A:Chem., 142, 77 (1999)].

Metal porphyrin catalysts are also reported to be active for the oxidation of isobutane and cumene. In the presence of oxygen these substrates form the hydroperoxide, which then decomposes to yield the alcohol and ketone. The oxidation of n-dodecane with cumene hydroperoxide or TBHP to detergent grade alcohols has been reported using Fe, Mn, Co porphyrin catalysts and mixtures [U.S. Pat. No. 4,978,799 (1990)]. Metal acetylacetonate complexes are reported to be active for the oxidation of isobutane and cumene. In the presence of oxygen these substrates form the hydroperoxide, which then decomposes to yield the alcohol/ketone products. The productions of detergent grade alcohols by the oxidation of n-dodecane with cumene hydroperoxide or TBHP have been reported using Fe, Ru and Cr acetyacetonate catalysts and their mixture [U.S. Pat. No. 4,978,800 (1990)]. In the presence of $RuCl_2(PPh_3)_3$, and TBHP, decane oxidation with 28% conversion has been observed. Ketones are the major product formed with 38% selectivity. The alcohol formation is about 2% [S. I. Murahashi, et al., Tetrahedron Lett., 34(8), 1299 (1993)]. U.S. Pat. No. 4,459,427 (1984) describes a process for the production of alcohol and ketone derivatives by reacting the linear or branched alkanes ($C_2$-$C_{20}$) with TBHP at ambient or elevated temperature and pressure in the presence of iron or manganese phthalocynine or porphyrin square planar complexes having heterocyclic nitrogen donor ligands, and where the complex has either no axial ligands, e.g. the lower valency or cationic complex, or has an axial ligand which is non-coordinating or weakly-coordinating. D. Mansuy et al. [Angew. Chem. Intl. Ed. Engl., 19 (11), 909 (1980)], describe the hydroxylation of cyclohexane and n-heptane by alkyl hydroperoxide using metalloporphyrin and in particular iron (111) and manganese (111) porphyrins in the form of Fe(tetraphenyl porphyrin)Cl and Mn(TPP)Cl. Ru/C has been used for the oxidation of different alkanes (cycloalkanes, n-heptane and n-decane) using TBHP and peracetic acid as the oxidants, to yield 72-90% of oxygenates (alcohol+ketones) [S. Murahashi, et al., J. Org. Chem., 65, 9186 (2000)].

The oxidation of cyclohexane, hexane and heptane to alcohols and ketones has also been reported using cis-[Ru (II)(L)$_2$—(OH$_2$)$_2$]$^{2+}$ complex catalysts (where L=substituted 2,2'-bipyridines of 1,10-phenanthrolines [T. Lau et al., J. Chem. Soc., Chem. Commun., 1406 (1988)].

Numerous heterogeneous catalysts have also been found to be active for the oxidation of alkanes. Co/Mn supported on different microporous aluminophosphates were used for the oxidation of dodecane with air at 100° C. [R. Raja and J. M. Thomas, Chem. Commun., (17), 1841 (1998)]. The highest conversion of dodecane reported was 5.5%. The products formed were $C_{12}$ alcohols, ketones and gaseous carbon oxides. The selectivity to alcohol and ketone was 35% and 20%, respectively. The selectivity for terminal alcohol and aldehyde was 37%.

In the literature, a number of researchers have reported that the detergent grade alcohols were obtained in high selectivity by the oxidation of higher alkanes using boric acid as a catalyst. A. N. Bashikirov, et al. [Proc. World Pet. Cong., Vol. 4 175 (1959)] have reported the synthesis of higher aliphatic alcohols by liquid phase oxidation of paraffinic hydrocarbons in the presence of boric acid and found that a high selectivity to alcohols can be achieved by proper selection of reaction conditions. Nippon Shokubai in Japan practices a commercial process for the manufacture of detergent alcohols by alkane oxidation in the presence of boric acid [U.S. Pat. No. 3,660,504 (1972)]. Here the diluted oxygen (5% in nitrogen) is used as the oxygen source and the alkyl hydroperoxides are formed in situ. These interact with the boric acid to form borate esters, which on hydrolysis yield the detergent alcohols. The conversion level for alkane is 31% with a selectivity of 72% to alcohols. No metal catalysts are used in this process. The boric acid serves as an esterification agent in the oxidation, which prevents them from further oxidation by interrupting the oxidative conversion chain at the alcohol stage. A similar observation has been reported by N. J. Stevens and J. R. Livingston "A New Route for Alcohols" [Chem. Eng. Progress, 64(7), 62 (1968)]. M. Iam and M. Hassan [(Ind. Eng. Chem. Prod. Res., 20, 315 (1981)] have reported that the direct oxidation of n-dodecane in the presence of boron compounds like tributoxyboroxine, boron trioxide, dibutoxyborane, etc. using dilute oxygen (4% $O_2$ in $N_2$) leads to a mixture of the six possible straight-chain $C_{12}$ alcohols.

U.S. Pat. No. 5,767,320 (Raja and Ratnasamy, 1998] describes a process for the oxidation of cyclohexane to a mixture of cyclohexanone and cyclohexanol using Fe, Co, Cu, Cr, Mn complex of phthalocynine or porphyrin and mixture as catalysts in which some or all of the hydrogen atoms of the phthalocynine or porphyrin have been replaced by electron withdrawing groups.

The above literature reveal that the production of alcohols and ketones by the oxidation of alkanes using homogeneous porphyrin, phthalocynine and similar planar complexes of metal like Fe, Co, Mn, Cu, Ru, Rh and supported catalysts in the presence of alkyl hydroperoxide [TBHP, CHP]. In the literature, there are no reports available on the co-oxidation involving alkanes and isoalkanes in presence of oxygen for the preparation of alcohols and ketones.

In the present invention provides a process for the preparation of a mixture of alcohols and ketones by liquid phase oxidation of isoalkanes to alkyl hydroperoxides with simultaneous transfer of oxygen to alkanes in presence of heterogeneous catalysts.

This invention provides a process by the use of a heterogeneous catalyst system, which can be separated from the reaction mixture with ease and reused for another reaction and also provides a process that is environmentally more benign.

OBJECTIVES OF THE INVENTION

The main object of the present invention is to provide a process for the preparation of a mixture of alcohols and ketones by liquid phase oxidation of isoalkanes to alkyl hydroperoxides with simultaneous transfer of oxygen to alkanes in presence of oxides alkaline earth and rare earth metal catalysts.

Yet another object of the present invention is to develop a process, which will be environmentally more benign.

Yet another object of the invention to provide a process for the preparation of a mixture of alcohols and ketones with minimum by-products formation.

Yet another object of this invention is that the process is operated in non-catalytic or by the use of solid oxides as catalysts Yet another object of the present invention is to use linear alkanes, which may be selected from $C_6$ to $C_{20}$ paraffins, preferably $C_{10}$ to $C_{16}$ paraffins.

Yet another object of the present invention is to use the isoalkanes to produce alkyl hydroperoxide, which may be selected from isobutane or isopentane, preferably isopentane.

Yet another object of this invention is to use the air or oxygen as an oxidant for the formation of alkyl hydroperoxide from isoalkanes.

Yet another object of this invention is to provide a process for the production of a mixture of alcohols and ketones at elevated temperature and pressure conditions.

SUMMARY OF THE INVENTION

The present invention provides a process for the production of a mixture of alcohols and ketones by liquid phase oxidation of isoalkanes to alkyl hydroperoxides with simultaneous transfer of oxygen to alkanes in presence of oxides of alkaline earth and rare earth metal catalysts.

The reactions were carried out at a temperature ranging between 110°-160° C. and air pressure ranging between 100-1500 psig in a high pressure Parr autoclave for a period of 0.5-20 h. After the reaction was completed, the reaction mixture was cooled to 5° C., filtered and the reactants and products were analyzed by gas chromatograph (GC). The products were also identified by gas chromatograph-mass spectroscopy (GCMS). The present invention produces a mixture of alcohols and ketones with high activity and selectivity along with other byproducts such as diketones and acids. The tertiary amyl alcohol has also been formed as a major decomposition product of tertiary amyl hydroperoxide.

DETAILED DESCRIPTION OF THE INVENTION

Accordingly, the present invention provides a process for the preparation of a mixture of alcohols and ketones, which comprises reacting a mixture of alkane and isoalkane with air or oxygen, optionally in the presence of heterogeneous catalyst for liquid phase oxidation of isoalkane ($C_4$ and $C_5$) to alkyl hydroperoxides with simultaneous transfer of oxygen to alkanes ($C_8$-$C_{20}$), at a temperature ranging between 110°-160° C. and air pressure ranging between 100-1500 psig, for a period of 0.5-20 hrs, cooling the above said reaction mixture to a temperature of about 5° C. and separating the desired products by known methods.

In an embodiment of the present invention the heterogeneous catalyst used is selected from oxides of alkaline earth metals and oxides of rare earth metals.

In yet another embodiment the oxide of alkaline earth metal used selected from the oxides of magnesium, calcium, barium, and strontium.

In yet another embodiment the oxide of rare earth metal used selected from the oxides of lanthanum, cerium, samarium, neodymium and europium.

In yet another embodiment the mole ratio of linear alkane to heterogeneous catalyst used is in the range of 0.5-100.

In yet another embodiment the mole ratio of alkane to isoalkane used is in the range of 0.05-50.

In yet another embodiment the isoalkane used is selected from isobutane and isopentane.

In yet another embodiment n and isoalkanes used in the mixture of n-alkane and isoalkanes are having the same carbon number.

In yet another embodiment the oxygen used is either pure oxygen or a mixture of 1-20% oxygen in nitrogen.

In yet another embodiment the reaction is carried out in the absence or presence of tertiary butyl hydroperoxide as an initiator.

In yet another embodiment the reaction is carried out in a semi-continuous way by dosing of the isoalkanes.

In yet another embodiment the reaction is carried out in a continuous reactor, with catalyst in a fixed bed.

In still another embodiment the catalyst used is reusable for several times for further reactions.

The novelty of the invention lies in the liquid phase oxidation of isoalkanes to alkyl hydroperoxides with simultaneous transfer of oxygen to alkanes for the preparation of a mixture of alcohols and ketones.

The following examples are given by the way of illustration and therefore should not be construed to limit the scope of the invention

EXAMPLE 1

A mixture of 55.0 ml dodecane and 5.0 ml isopentane was charged to the stirred autoclave of 300 ml capacity having a temperature and pressure controller and water condenser. The reaction vessel was heated to 140° C. and then pressurized the reactor up to 850 psig with air and continued the reaction for 4 h. The reactor was refilled with oxygen by taking into account the absorbed oxygen in the reactor and the reaction further continued up to 6 h. At the end of the reaction, the reaction mixture was cooled to 5° C. The reactants and products were analyzed by gas chromatograph and the products were also identified by gas chromatography mass spectrometry. The GC analysis of reaction mixture showed 28.2% conversion of dodecane with and 45.4% and 15.7% selectivity to dodecanone and dodecanol, respectively. Acids were formed as major side products with 38.9% selectivity.

EXAMPLE 2

A mixture of 60.0 ml dodecane was charged to the stirred autoclave of 300 ml capacity having a temperature and pressure controller and water condenser. The reaction vessel was heated to 140° C. and then pressurized the reactor up to 850 psig with air and continued the reaction for 4 h. The reactor was refilled with oxygen by taking into account the absorbed oxygen in the reactor and the reaction further continued up to 6 h. At the end of the reaction, the reaction mixture was cooled to 5° C. The reactants and products were analyzed by gas chromatograph and the products were also identified by gas chromatography mass spectrometry. The GC analysis of reaction mixture showed 19.3% conversion of dodecane with 49.1% and 17.2% selectivity to dodecanone and dodecanol, respectively. Acids were formed as major side products with 33.4% selectivity.

EXAMPLE 3

A mixture of 60.0 ml dodecane and 5.0 ml isopentane was charged to the stirred autoclave of 300 ml capacity having a temperature and pressure controller and water condenser. The reaction vessel was heated to 120° C. and then pressurized the reactor up to 850 psig with air and continued the reaction for 4 h. The reactor was refilled with oxygen by taking into account the absorbed oxygen in the reactor and the reaction further continued up to 6 h. At the end of the reaction, the reaction mixture was cooled to 5° C. The reactants and products were analyzed by gas chromatograph and the products were also identified by gas chromatography mass spectrometry. The GC analysis of reaction mixture showed 17.8% conversion of dodecane with 49.1% and 23.8% selectivity to dodecanone and dodecanol, respectively. Acids were formed as major side products with 27.1% selectivity.

EXAMPLE 4

A mixture of 60.0 ml dodecane and 5.0 ml isopentane was charged to the stirred autoclave of 300 ml capacity having a temperature and pressure controller and water condenser. The reaction vessel was heated to 110° C. and then pressurized the reactor up to 850 psig with air and continued the reaction for 4 h. The reactor was refilled with oxygen by taking into account the absorbed oxygen in the reactor and the reaction further continued up to 6 h. At the end of the reaction, the reaction mixture was cooled to 5° C. The reactants and products were analyzed by gas chromatograph and the products were also identified by gas chromatography mass spectrometry. The GC analysis of reaction mixture showed 4.1% conversion of dodecane with 52.4% and 15.9% selectivity to dodecanone and dodecanol, respectively. Acids were formed as major side products with 31.6% selectivity.

EXAMPLE 5

A mixture of 60.0 ml dodecane and 1.0 g MgO was charged to the stirred autoclave of 300 ml capacity having a temperature and pressure controller and water condenser. The reaction vessel was heated to 140° C. and then pressurized the reactor up to 850 psig with air and continued the reaction for 4 h. The reactor was refilled with oxygen by taking into account the absorbed oxygen in the reactor and the reaction further continued up to 6 h. At the end of the reaction, the reaction mixture was cooled to 5° C., filtered to separate the catalyst, and then weighed. The reactants and products were analyzed by gas chromatograph and the products were also identified by gas chromatography mass spectrometry. The GC analysis of reaction mixture showed 3.4% conversion of dodecane with 35.0% and 32.1% selectivity to dodecanone and dodecanol, respectively. Acids were formed as major side products with 32.9% selectivity.

EXAMPLE 6

A mixture of 55.0 ml dodecane, 5.0 ml isopentane and 1.0 g MgO was charged to the stirred autoclave of 300 ml capacity having a temperature and pressure controller and water condenser. The reaction vessel was heated to 140° C. and then pressurized the reactor up to 850 psig with air and continued the reaction for 4 h. The reactor was refilled with oxygen by taking into account the absorbed oxygen in the reactor and the reaction further continued up to 6 h. At the end of the reaction, the reaction mixture was cooled to 5° C., filtered to separate the catalyst, and then weighed. The reactants and products were analyzed by gas chromatograph and the products were also identified by gas chromatography mass spectrometry. The GC analysis of reaction mixture showed 12.3% conversion of dodecane with 42.0% and 26.3% selectivity to dodecanone and dodecanol, respectively. Acids were formed as major side products with 31.7% selectivity.

EXAMPLE 7

A mixture of 55.0 ml dodecane, 5.0 ml isopentane, 1.0 ml TBHP (DTBP) and 1.0 g MgO was charged to the stirred autoclave of 300 ml capacity having a temperature and pressure controller and water condenser. The reaction vessel was heated to 140° C. and then pressurized the reactor up to 850 psig with air and continued the reaction for 4 h. The reactor was refilled with oxygen by taking into account the absorbed oxygen in the reactor and the reaction further continued up to 6 h. At the end of the reaction, the reaction mixture was cooled to 5° C., filtered to separate the catalyst, and then weighed. The reactants and products were analyzed by gas chromatograph and the products were also identified by gas chromatography mass spectrometry. The GC analysis of reaction mixture showed 25.3% conversion of dodecane with 38.8% and 31.3% selectivity to dodecanone and dodecanol, respectively. Acids were formed as major side products with 30.0% selectivity.

EXAMPLE 8

A mixture of liner alkanes ($C_{10}$-$C_{14}$) 60.0 ml was charged to the stirred autoclave of 300 ml capacity having a temperature and pressure controller and water condenser. The reaction vessel was heated to 140° C. and then pressurized the reactor up to 850 psig with air and continued the reaction for 4 h. The reactor was refilled with oxygen by taking into account the absorbed oxygen in the reactor and the reaction further continued up to 6 h. At the end of the reaction, the reaction mixture was cooled to 5° C. The reactants and products were analyzed by gas chromatograph and the products were also identified by gas chromatography mass spectrometry. The GC analysis of reaction mixture showed 17.8% conversion of dodecane with 89.4% selectivity to products such as alcohols, ketones and acids.

EXAMPLE 9

A mixture liner alkanes ($C_{10}$-$C_{14}$) 55.0 ml, 5.0 ml isopentane and 1.0 ml TBHP (DTBP) was charged to the stirred autoclave of 300 ml capacity having a temperature and pressure controller and water condenser. The reaction vessel was heated to 140° C. and then pressurized the reactor up to 850 psig with air and continued the reaction for 4 h. The reactor was refilled with oxygen by taking into account the absorbed oxygen in the reactor and the reaction further continued up to 6 h. At the end of the reaction, the reaction mixture was cooled to 5° C. The reactants and products were analyzed by gas chromatograph and the products were also identified by gas chromatography mass spectrometry. The GC analysis of reaction mixture showed 28.0% conversion alkanes with 92.6% selectivity to products such as alcohols, ketones and acids.

EXAMPLE 10

A mixture of 55.0 ml dodecane, 5.0 ml isopentane and 1.0 g CaO was charged to the stirred autoclave of 300 ml capacity having a temperature and pressure controller and water condenser. The reaction vessel was heated to 140° C. and then pressurized the reactor up to 850 psig with air and continued the reaction for 4 h. The reactor was refilled with oxygen by taking into account the absorbed oxygen in the reactor and the reaction further continued up to 6 h. At the end of the reaction, the reaction mixture was cooled to 5° C., filtered to separate the catalyst, and then weighed. The reactants and products were analyzed by gas chromatograph and the products were also identified by gas chromatography mass spectrometry. The GC analysis of reaction mixture showed 9.3% conversion of dodecane with 17.9% and 32.3% selectivity to dodecanone and dodecanol, respectively. Acids were formed as major side products with 49.8% selectivity.

EXAMPLE 11

A mixture of 55.0 ml dodecane, 5.0 ml isopentane and 1.0 g SrO was charged to the stirred autoclave of 300 ml capacity having a temperature and pressure controller and water condenser. The reaction vessel was heated to 140° C. and then pressurized the reactor up to 850 psig with air and continued the reaction for 4 h. The reactor was refilled with oxygen by taking into account the absorbed oxygen in the reactor and the reaction further continued up to 6 h. At the end of the reaction, the reaction mixture was cooled to 5° C., filtered to separate the catalyst, and then weighed. The reactants and products were analyzed by gas chromatograph and the products were also identified by gas chromatography mass spectrometry. The GC analysis of reaction mixture showed 19.1% conversion of dodecane with 42.5% and 18.7% selectivity to dodecanone and dodecanol, respectively. Acids were formed as major side products with 38.8% selectivity.

EXAMPLE 12

A mixture of 55.0 ml dodecane, 5.0 ml isopentane and 1.0 g BaO was charged to the stirred autoclave of 300 ml capacity having a temperature and pressure controller and water condenser. The reaction vessel was heated to 140° C. and then pressurized the reactor up to 850 psig with air and continued the reaction for 4 h. The reactor was refilled with oxygen by taking into account the absorbed oxygen in the reactor and the reaction further continued up to 6 h. At the end of the reaction, the reaction mixture was cooled to 5° C., filtered to separate the catalyst, and then weighed. The reactants and products were analyzed by gas chromatograph and the products were also identified by gas chromatography mass spectrometry. The GC analysis of reaction mixture showed 16.7% conversion of dodecane with 37.6% and 21.2% selectivity to dodecanone and dodecanol, respectively. Acids were formed as major side products with 41.2% selectivity.

EXAMPLE 13

A mixture of 55.0 ml dodecane, 5.0 ml isopentane and 1.0 g $La_2O_3$ was charged to the stirred autoclave of 300 ml capacity having a temperature and pressure controller and water condenser. The reaction vessel was heated to 140° C. and then pressurized the reactor up to 850 psig with air and continued the reaction for 4 h. The reactor was refilled with oxygen by taking into account the absorbed oxygen in the reactor and the reaction further continued up to 6 h. At the end of the reaction, the reaction mixture was cooled to 5° C., filtered to separate the catalyst, and then weighed. The reactants and products were analyzed by gas chromatograph and the products were also identified by gas chromatography mass spectrometry. The GC analysis of reaction mixture showed 11.8% conversion of dodecane with 17.3% and 30.1% selectivity to dodecanone and dodecanol, respectively. Acids were formed as major side products with 52.6% selectivity.

EXAMPLE 14

A mixture of 55 ml dodecane, 5 ml isopentane, 1.0 ml TBHP (DTBP) and 1.0 g CaO was charged to the stirred autoclave of 300 ml capacity having a temperature and pressure controller and water condenser. The reaction vessel was heated to 140° C. and then pressurized the reactor up to 850 psig with air and continued the reaction for 4 h. The reactor was refilled with oxygen by taking into account the absorbed oxygen in the reactor and the reaction further continued up to 6 h. At the end of the reaction, the reaction mixture was cooled to 5° C., filtered to separate the catalyst, and then weighed. The reactants and products were analyzed by gas chromatograph and the products were also identified by gas chromatography mass spectrometry. The GC analysis of reaction mixture showed 23.3% conversion of dodecane with 24.0% and 29.8% selectivity to dodecanone and dodecanol, respectively. Acids were formed as major side products with 46.3% selectivity.

EXAMPLE 15

A mixture of 55 ml dodecane, 5 ml isopentane, 1.0 ml TBHP (DTBP) and 1.0 g SrO was charged to the stirred autoclave of 300 ml capacity having a temperature and pressure controller and water condenser. The reaction vessel was heated to 140° C. and then pressurized the reactor up to 850 psig with air and continued the reaction for 4 h. The reactor was refilled with oxygen by taking into account the absorbed oxygen in the reactor and the reaction further continued up to 6 h. At the end of the reaction, the reaction mixture was cooled to 5° C., filtered to separate the catalyst, and then weighed. The reactants and products were analyzed by gas chromatograph and the products were also identified by gas chromatography mass spectrometry. The GC analysis of reaction mixture showed 39.9% conversion of dodecane with 40.2% and 18.9% selectivity to dodecanone and dodecanol, respectively. Acids were formed as major side products with 40.9% selectivity.

EXAMPLE 16

A mixture of 55 ml dodecane, 5 ml isopentane, 1.0 ml TBHP (DTBP) and 1.0 g BaO was charged to the stirred autoclave of 300 ml capacity having a temperature and pressure controller and water condenser. The reaction vessel was heated to 140° C. and then pressurized the reactor up to 850 psig with air and continued the reaction for 4 h. The reactor was refilled with oxygen by taking into account the absorbed oxygen in the reactor and the reaction further continued up to 6 h. At the end of the reaction, the reaction mixture was cooled to 5° C., filtered to separate the catalyst, and then weighed. The reactants and products were analyzed by gas chromatograph and the products were also identified by gas chromatography mass spectrometry. The GC analysis of reaction mixture showed 35.5% conversion of dodecane with 46.2% and 22.1% selectivity to dodecanone and dodecanol, respectively. Acids were formed as major side products with 31.7% selectivity.

EXAMPLE 17

A mixture of 55 ml dodecane, 5 ml isopentane, 1.0 ml TBHP (DTBP) and 1.0 g $La_2O_3$ was charged to the stirred autoclave of 300 ml capacity having a temperature and pressure controller and water condenser. The reaction vessel was heated to 140° C. and then pressurized the reactor up to 850 psig with air and continued the reaction for 4 h. The reactor was refilled with oxygen by taking into account the absorbed oxygen in the reactor and the reaction further continued up to 6 h. At the end of the reaction, the reaction mixture was cooled to 5° C., filtered to separate the catalyst, and then weighed. The reactants and products were analyzed by gas chromatograph and the products were also identified by gas chromatography mass spectrometry. The GC analysis of reaction mixture showed 32.8% conversion of dodecane with 34.0% and 24.3% selectivity to dodecanone and dodecanol, respectively. Acids were formed as major side products with 41.7% selectivity.

EXAMPLE 18

A mixture of 55 ml decane and 5 ml isopentane was charged to the stirred autoclave of 300 ml capacity having a temperature and pressure controller and water condenser. The reaction vessel was heated to 140° C. and then pressurized the reactor up to 850 psig with air and continued the reaction for 4 h. The reactor was refilled with oxygen by taking into account the absorbed oxygen in the reactor and the reaction further continued up to 6 h. At the end of the reaction, the reaction mixture was cooled to 5° C. The reactants and products were analyzed by gas chromatograph and the products were also identified by gas chromatography mass spectrometry. The GC analysis of reaction mixture showed 17.8% conversion of decane with 49.5% and 18.8% selectivity to decanone and decanol, respectively. Acids were formed as major side products with 31.7% selectivity.

EXAMPLE 19

A mixture of 55 ml hexadecane and 5 ml isopentane was charged to the stirred autoclave of 300 ml capacity having a temperature and pressure controller and water condenser. The reaction vessel was heated to 140° C. and then pressurized the reactor up to 850 psig with air and continued the reaction for 4 h. The reactor was refilled with oxygen by taking into account the absorbed oxygen in the reactor and the reaction further continued up to 6 h. At the end of the reaction, the reaction mixture was cooled to 5° C. The reactants and products were analyzed by gas chromatograph and the products were also identified by gas chromatography mass spectrometry. The GC analysis of reaction mixture showed 36.6% conversion of hexadecane with 48.9% and 17.8% selectivity to hexadecanone and hexadecanol, respectively. Acids were formed as major side products with 33.2% selectivity.

EXAMPLE 20

A mixture of 58.0 ml dodecane, 2.0 ml isopentane, 1.0 ml TBHP (DTBP) and 1.0 g MgO was charged to the stirred autoclave of 300 ml capacity having a temperature and pressure controller and water condenser. The reaction vessel was heated to 140° C. and then pressurized the reactor up to 850 psig with air and continued the reaction for 4 h. The reactor was refilled with oxygen by taking into account the absorbed oxygen in the reactor and the reaction further continued up to 6 h. At the end of the reaction, the reaction mixture was cooled to 5° C., filtered to separate the catalyst, and then weighed. The reactants and products were analyzed by gas chromatograph and the products were also identified by gas chromatography mass spectrometry. The GC analysis of reaction mixture showed 34.9% conversion of dodecane with 39.2% and 16.3% selectivity to dodecanone and dodecanol, respectively. Acids were formed as major side products with 44.6% selectivity.

EXAMPLE 21

A mixture of 40 ml dodecane, 20 ml isopentane, 1.0 ml TBHP (DTBP) and 1.0 g MgO was charged to the stirred autoclave of 300 ml capacity having a temperature and pressure controller and water condenser. The reaction vessel was heated to 140° C. and then pressurized the reactor up to 850 psig with air and continued the reaction for 4 h. The reactor was refilled with oxygen by taking into account the absorbed oxygen in the reactor and the reaction further continued up to 6 h. At the end of the reaction, the reaction mixture was cooled to 5° C., filtered to separate the catalyst, and then weighed. The reactants and products were analyzed by gas chromatograph and the products were also identified by gas chromatography mass spectrometry. The GC analysis of reaction mixture showed 18.9% conversion of dodecane with 42.5% and 27.6% selectivity to dodecanone and dodecanol, respectively. Acids were formed as major side products with 29.9% selectivity.

EXAMPLE 22

A mixture of 55 ml dodecane, 5 ml isopentane, 1.0 ml TBHP (DTBP) and 3.0 g MgO was charged to the stirred autoclave of 300 ml capacity having a temperature and pressure controller and water condenser. The reaction vessel was heated to 140° C. and then pressurized the reactor up to 850 psig with air and continued the reaction for 4 h. The reactor was refilled with oxygen by taking into account the absorbed oxygen in the reactor and the reaction further continued up to 6 h. At the end of the reaction, the reaction mixture was cooled to 5° C., filtered to separate the catalyst, and then weighed. The reactants and products were analyzed by gas chromatograph and the products were also identified by gas chromatography mass spectrometry. The GC analysis of reaction mixture showed 24.9% conversion of dodecane with 40.1% and 21.7% selectivity to dodecanone and dodecanol, respectively. Acids were formed as major side products with 38.3% selectivity.

EXAMPLE 23

A mixture of 50 ml dodecane, 5 ml n-pentane and 5 ml isopentane, 1.0 ml TBHP (DTBP) and 1.0 g MgO was charged to the stirred autoclave of 300 ml capacity having a temperature and pressure controller and water condenser. The reaction vessel was heated to 140° C. and then pressurized the reactor up to 850 psig with air and continued the reaction for 4 h. The reactor was refilled with oxygen by taking into account the absorbed oxygen in the reactor and the reaction further continued up to 6 h. At the end of the reaction, the reaction mixture was cooled to 5° C., filtered to separate the catalyst, and then weighed. The reactants and products were analyzed by gas chromatograph and the products were also identified by gas chromatography mass spectrometry. The GC analysis of reaction mixture showed 35.5% conversion of dodecane with 41.4% and 21.5% selectivity to dodecanone and dodecanol, respectively. Acids were formed as major side products with 37.1% selectivity.

EXAMPLE 24

A mixture of 50 ml dodecane, 5 ml n-pentane and 5 ml isopentane, 1.0 ml TBHP (DTBP) and 1.0 g CaO was charged to the stirred autoclave of 300 ml capacity having a temperature and pressure controller and water condenser. The reaction vessel was heated to 140° C. and then pressurized the reactor up to 850 psig with air and continued the reaction for 4 h. The reactor was refilled with oxygen by taking into account the absorbed oxygen in the reactor and the reaction further continued up to 6 h. At the end of the reaction, the reaction mixture was cooled to 5° C., filtered to separate the catalyst, and then weighed. The reactants and products were analyzed by gas chromatograph and the products were also identified by gas chromatography mass spectrometry. The GC analysis of reaction mixture showed 19.3% conversion of dodecane with 23.2% and 32.6% selectivity to dodecanone and dodecanol, respectively. Acids were formed as major side products with 44.2% selectivity.

EXAMPLE 25

A mixture of 50 ml dodecane, 5 ml n-pentane and 5 ml isopentane, 1.0 ml TBHP (DTBP) and 1.0 g $La_2O_3$ was charged to the stirred autoclave of 300 ml capacity having a temperature and pressure controller and water condenser. The reaction vessel was heated to 140° C. and then pressurized the reactor up to 850 psig with air and continued the reaction for 4 h. The reactor was refilled with oxygen by taking into account the absorbed oxygen in the reactor and the reaction further continued up to 6 h. At the end of the reaction, the reaction mixture was cooled to 5° C., filtered to separate the catalyst, and then weighed. The reactants and products were analyzed by gas chromatograph and the products were also identified by gas chromatography mass spectrometry. The GC analysis of reaction mixture showed 33.1% conversion of dodecane with 33.2% and 22.4% selectivity to dodecanone and dodecanol, respectively. Acids were formed as major side products with 44.4% selectivity.

EXAMPLE 26

A mixture of 55 ml dodecane, 5 ml isopentane, 1.0 ml TBHP (DTBP) and 1.0 g MgO was charged to the stirred autoclave of 300 ml capacity having a temperature and pressure controller and water condenser. The reaction vessel was heated to 160° C. and then pressurized the reactor up to 850 psig with air and continued the reaction for 4 h. The reactor was refilled with oxygen by taking into account the absorbed oxygen in the reactor and the reaction further continued up to 6 h. At the end of the reaction, the reaction mixture was cooled to 5° C., filtered to separate the catalyst, and then weighed. The reactants and products were analyzed by gas chromatograph and the products were also identified by gas chromatography mass spectrometry. The GC analysis of reaction mixture showed 34.2% conversion of dodecane with 37.4% and 30.0% selectivity to dodecanone and dodecanol, respectively. Acids were formed as major side products with 32.6% selectivity.

Recycle Studies

EXAMPLE 27

A mixture of 55.0 ml dodecane, 5.0 ml isopentane, 1.0 ml TBHP (DTBP) and 1.0 g MgO (recovered catalyst from Example 7) was charged to the stirred autoclave of 300 ml capacity having a temperature and pressure controller and water condenser. The reaction vessel was heated to 140° C. and then pressurized the reactor up to 850 psig with air and continued the reaction for 4 h. The reactor was refilled with oxygen by taking into account the absorbed oxygen in the reactor and the reaction further continued up to 6 h. At the end of the reaction, the reaction mixture was cooled to 5° C., filtered to separate the catalyst, and then weighed. The reactants and products were analyzed by gas chromatograph and the products were also identified by gas chromatography mass spectrometry. The GC analysis of reaction mixture showed 26.2% conversion of dodecane with 37.9% and 32.5% selectivity to dodecanone and dodecanol, respectively. Acids were formed as major side products with 28.1% selectivity.

The Advantages of the Present Invention are

1. The present invention provides a process for the preparation of a mixture of alcohols and ketones via liquid phase oxidation of isopentane or a mixture of n-pentane and isopentane to alkyl hydroperoxides with simultaneous transfer of oxygen to alkanes using heterogeneous catalysts system.
2. The major advantage of the process is that the reaction conducted using a mixture of alkanes and isoalkanes with or without the catalysts in presence of air and hence an additional step for the production of alkyl hydroperoxide from isoalkanes is avoided.
3. Ketone/alcohol ratio is improved using the alkaline earth oxide or rare earth oxide catalysts.
4. The catalyst system reported in the present invention is heterogeneous catalysts system, which can be separated from the reaction mixture with ease and recycled for another reactions and hence the process, is more economic.

The invention claimed is:

1. A process for the preparation of a mixture of alcohols and ketones, which comprises reacting a mixture of alkane and isoalkane with air or oxygen, optionally in the presence of heterogeneous catalyst for liquid phase oxidation of isoalkane ($C_4$ and $C_5$) to alkyl hydroperoxides with simultaneous transfer of oxygen to alkanes ($C_8$-$C_{20}$), at a temperature ranging between 110°-160° C. and air pressure ranging between 100-1500 psig, for a period of 0.5-20 hrs, cooling the above said reaction mixture to a temperature of about 5° C. and separating the desired products by known methods.

2. A process according to claim 1, wherein the heterogeneous catalyst used is selected from oxides of alkaline earth metals and oxides of rare earth metals.

3. A process according to claim 2, wherein the oxide of alkaline earth metal used selected from the oxides of magnesium, calcium, barium, and strontium.

4. A process according to claim 2, wherein the oxide of rare earth metal used selected from the oxides of lanthanum, cerium, samarium, neodymium and europium.

5. A process according to claim 1, wherein the mole ratio of linear alkane to heterogeneous catalyst used is in the range of 0.5-100.

6. A process according to claim 1, wherein the mole ratio of alkane to isoalkane used is in the range of 0.05-50.

7. A process according to claim 1, wherein the isoalkane used is selected from isobutane and isopentane.

8. A process according to claim 1, wherein n and isoalkanes used in the mixture of n-alkane and isoalkanes are having the same carbon number.

9. A process according to claim 1, wherein the oxygen used is either pure oxygen or a mixture of 1-20% oxygen in nitrogen.

10. A process according to claim 1, wherein the reaction is carried out in the absence or presence of tertiary butyl hydroperoxide as an initiator.

11. A process according to claim 1, wherein the reaction is carried out in a semi-continuous way by dosing of the isoalkanes.

12. A process according to claim 1, wherein the reaction is carried out in a continuous reactor, with catalyst in a fixed bed.

13. A process according to claim 1, wherein the catalyst used is reusable for several times for further reactions.

* * * * *